United States Patent [19]
Zobel

[11] Patent Number: 5,725,585
[45] Date of Patent: Mar. 10, 1998

[54] ANATOMICALLY CORRECT GREAT TOE IMPLANT AND SURGICAL PROCEDURE FOR IMPLANTING THE SAME

[76] Inventor: Robert A. Zobel, 333 E. Downing, Mesa, Ariz. 85213

[21] Appl. No.: 807,758

[22] Filed: Feb. 27, 1997

[51] Int. Cl.[6] .................................................. A61F 2/42
[52] U.S. Cl. ............................................................ 623/21
[58] Field of Search ................................ 623/16, 18, 20, 623/21

[56] References Cited

U.S. PATENT DOCUMENTS

| | | | |
|---|---|---|---|
| D. 277,509 | 2/1985 | Lawrence et al. | D24/33 |
| D. 277,784 | 2/1985 | Sgarlato et al. | D24/33 |
| D. 284,099 | 6/1986 | Laporta et al. | D24/33 |
| D. 291,731 | 9/1987 | Aikins | D24/33 |
| 3,593,342 | 7/1971 | Niebauer et al. | 3/1 |
| 3,651,521 | 3/1972 | Devas | 3/1 |
| 3,992,726 | 11/1976 | Freeman et al. | 3/1.91 |
| 4,213,208 | 7/1980 | Marne | 3/1.91 |
| 4,634,445 | 1/1987 | Helal | 623/21 |
| 4,685,919 | 8/1987 | Niwa et al. | 623/21 |
| 4,731,087 | 3/1988 | Sculco et al. | 623/21 |
| 4,787,908 | 11/1988 | Wyss et al. | 623/21 |
| 4,908,031 | 3/1990 | Frisch | 623/21 |
| 5,037,440 | 8/1991 | Koenig | 623/21 |
| 5,207,712 | 5/1993 | Cohen | 623/21 |
| 5,314,486 | 5/1994 | Zang et al. | 623/21 |
| 5,326,366 | 7/1994 | Pascarella et al. | 623/21 |
| 5,458,648 | 10/1995 | Berman et al. | 623/21 |
| 5,609,641 | 3/1997 | Johnson et al. | 623/18 X |

FOREIGN PATENT DOCUMENTS

| | | | |
|---|---|---|---|
| 0201651 | 11/1986 | European Pat. Off. | A61F 2/42 |
| 2651119 | 1/1991 | France | A61F 2/42 |
| 9200709 | 1/1992 | WIPO | 623/21 |

*Primary Examiner*—Mary Beth Jones
*Attorney, Agent, or Firm*—Martin & Associates; Derek P. Martin

[57] ABSTRACT

A great toe implant for replacement of a portion of the proximal phalanx has a substantially reniform bearing surface, providing a recess on the lower edge for receiving the flexor hallucis longus tendon once implanted. Retaining portions (such as small spikes) provided on the rear face of the implant engage the proximal phalanx, preventing rotation of the implant with respect to the proximal phalanx once the implant is surgically implanted. In addition, holes are provided on the lower edge of the implant to attach the implant to the flexor hallucis brevis tendons and to the proximal phalanx.

9 Claims, 3 Drawing Sheets

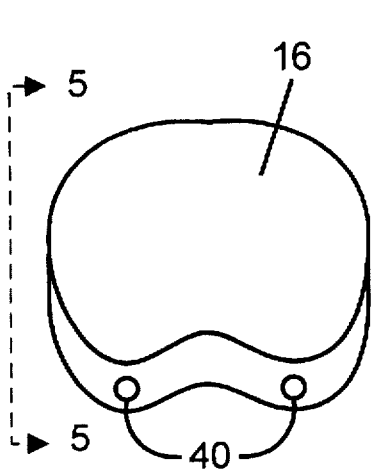
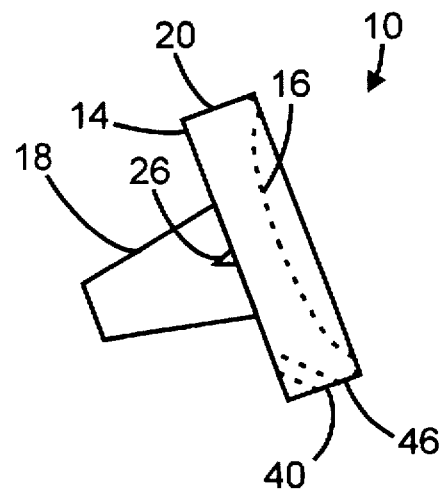
FIG. 4  FIG. 5
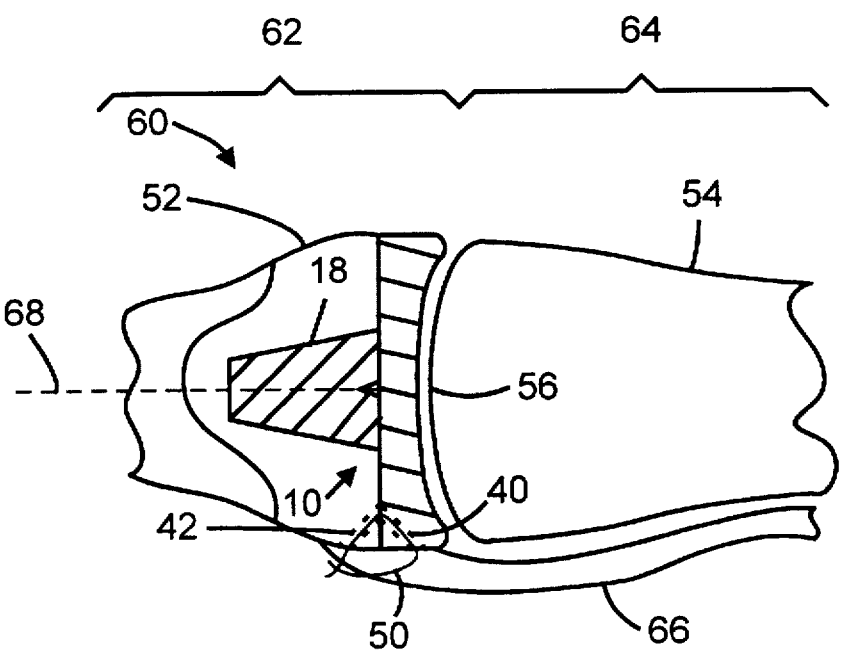
FIG. 6

ANATOMICALLY CORRECT GREAT TOE IMPLANT AND SURGICAL PROCEDURE FOR IMPLANTING THE SAME

BACKGROUND OF THE INVENTION

1. Field of the Invention

The present invention generally relates to prosthetic devices for surgical joint replacement. More specifically, the invention relates to a toe implant and surgical procedure for replacing a portion of a human great toe joint.

2. Description of the Prior Art

The medical profession has used prosthetic devices for years to replace defective natural joints. One joint that is commonly replaced with a prosthetic device (i.e., implant) is the great toe (i.e., big toe) joint. Initially, hemi-joint replacements for the big toe were made of silicone taking advantage of the firm but resilient nature of the material. This method used a prosthetic device attached to the phalanx when the phalanx cartilage was degenerated but the metatarsal head was still intact. However, it was found that silicone was too soft for this intended purpose. The silicone surface breaks into small particles that are transported into the lymph system. With the recent concerns over the damaging effects of silicone in the human body that arose from documented problems with silicone breast implants, using silicone implants for hemi-joint replacement is no longer a preferred solution.

Another method, similar to the hemi-joint silicone replacement, is total joint replacement, also using silicone. An implant for total joint replacement of the big toe has one end that is attached to the metatarsal while the other end is attached to the phalanx, and has a hinge between the two ends. This method was typically used when both the phalanx cartilage and the metatarsal head had been degenerated. Although this method has found limited success, it has been found that this method is not acceptable for all users, particularly those who propel off their big toe while walking or running, which commonly occurs during athletic activities. In addition, the concerns discussed above regarding the potential damaging effects of silicone in the body have caused medical practitioners to search for alternative materials.

Metal prosthetic implant devices, typically made of titanium or a titanium alloy, eliminate the health concerns of using silicone devices. When using metal prosthetic implants, either one or both sides of the joint are fitted with a metal implant. When a metal piece is used on only one side of the joint, it has been found that the head of the remaining natural joint wears out faster than the metal implant. Moreover, if both sides of the joint are replaced by the metal implants, then it has been found that there is a slow unavoidable dislocation of the joint (known as subluxation) and that there have been problems with increased joint stiffness.

Hemi-joint replacement is generally preferred over full joint replacement when the proximal phalanx in the great toe joint has deteriorated but the metatarsal head is still relatively intact. In this case, only a portion of the proximal phalanx is replaced. A variety of different toe implants have been developed for this purpose. One example of a great toe implant for replacing a portion of the proximal phalanx is disclosed in U.S. Pat. No. 5,326,366 "Biomechanical Great Toe Implant", (issued Jul. 5, 1994 to Pascerella et al. and assigned to Wright Medical Technology, Inc.), which is incorporated herein by reference. The Pascerella implant device has a concave bearing surface that has the shape of an internal segment of a sphere, providing a substantially round or elliptical perimeter to the bearing surface.

Complete joint replacement may be accomplished using a variety of prior art implants. Example of total joint implants include: U.S. Pat. No. 5,458,648 "Great Toe Implant and Method of Implantation" (issued Oct. 17, 1995 to Berman et al. and assigned to Kinetikos Medical, Inc.); U.S. Pat. No. 5,314,486 "Non-Constrained Total Joint System" (issued May 24, 1994 to Zang et al. and assigned to MicroAire Surgical Instruments, Inc.); U.S. Pat. No. 5,037,440 "Orthopedic Toe Implant" (issued Aug. 6, 1991 to Koenig and assigned to Koenig Implant, Inc.); U.S. Pat. No. 4,908,031 "Toe Implant" (issued Mar. 13, 1990 to Frisch and assigned to Dow Corning Wright); and E.P. Patent No. 0 201 651 A1 "Prosthetic Implant for Metatarsal-Phalangeal Joint and Cutting Device Used for its Positioning" (issued Nov. 20, 1986 to Lelievre et at.). All of the patents listed above are incorporated herein by reference.

Each of the prior art patents cited herein show a phalangeal component that has a concave bearing surface that is generally in the shape of an internal segment of a sphere, providing a substantially circular or elliptical perimeter to the bearing surface. However, the natural bearing surface on a proximal phalanx does not have a circular or elliptical perimeter. Therefore, the prior art implants do not provide an optimal solution because they are not anatomically correct.

In addition, some prior art implants may be subject to rotating on the proximal phalanx once surgically implanted. Others have a stem configuration that prevents rotation. For example, many of the prior art implants have stems that are substantially square or rectangular in cross-section, requiring the surgeon to flatten the sides of the cavity formed in the proximal phalanx to receive the implant. While implants with a square or rectangular stem will not rotate once implanted, obtaining a cavity that closely fits the implant stem and that places the implant in the correct rotational position requires a great deal of precision, expertise, and care.

Furthermore, prior art implants are typically attached to the bone, but have no way of being attached to the neighboring tendons. Therefore, there existed a need to provide a great toe implant that has an anatomically correct reniform bearing surface, thereby providing an implant that will more closely simulate the natural joint. In addition, the implant should be easier for the surgeon to align in the proper rotational position. Furthermore, the implant should provide a way of attaching the implant to neighboring tendons to enhance the integrity of the prosthetic joint.

SUMMARY OF THE PREFERRED EMBODIMENTS OF THE INVENTION

According to a preferred embodiment of the invention, a great toe implant for replacement of a portion of the proximal phalanx has a substantially reniform bearing surface, providing a recess on the lower edge for receiving the flexor hallucis longus tendon once implanted. Retaining portions (such as small spikes) provided on the rear face of the implant engage the proximal phalanx, preventing rotation of the implant with respect to the proximal phalanx once the implant is surgically implanted. In addition, holes are provided on the lower edge of the implant to attach the implant to the flexor hallucis brevis tendons and to the proximal phalanx.

There has thus been outlined, rather broadly, the summary of the preferred embodiments of the invention in order that the detailed description that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, neither is it intended to be limiting as to the scope of the invention in any way.

Other features of the present invention will become more clear from the following detailed description of the invention, taken in conjunction with the accompanying drawings and claims, or may be learned by the practice of the invention.

BRIEF DESCRIPTION OF THE DRAWINGS

The preferred exemplary embodiments of the present invention will hereinafter be described in conjunction with the appended drawings, where like designations denote like elements, and:

FIG. 4 is a perspective view of the implant of FIG. 1 showing the lower edge of the implant of FIG. 1;

FIG. 5 is side view of the implant of FIG. 4 taken along the line 5—5;

FIG. 6 is a partial cut-away skeletal representation of a side view of a great toe joint implant in accordance with the present invention when surgically implanted in the proximal phalanx.

Figure 1:
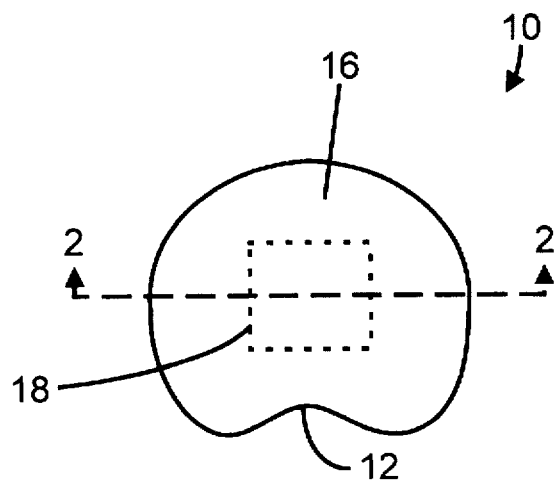
FIG. 1 is a front view of a great me implant in accordance with the present invention.

It is noted that the drawings of the invention are not to scale. The drawings are merely schematic representations, not intended to portray specific parameters of the invention. The drawings are intended to depict only typical embodiments of the preferred embodiments of the invention, and therefore should not be considered as limiting the scope of the invention. The invention will be described below with additional specificity and detail through the use of the accompanying drawings.

DETAILED DESCRIPTION OF PREFERRED EXEMPLARY EMBODIMENTS

A prosthetic implant for a portion of a proximal phalanx in a great toe joint according to the preferred exemplary embodiments disclosed herein has an anatomically correct reniform (i.e., kidney-shaped) bearing surface that provides a recess for the flexor hallucis longus tendon. In addition, the preferred embodiment includes retaining portions that engage the proximal phalanx and hold the implant in the correct rotational orientation. Furthermore, the preferred embodiment includes one or more holes that extend from the side wall of the implant to the rear face of the implant. When a hole is drilled in the proximal phalanx that lines up with the hole in the implant, surgical suture material may be passed through the holes and sutured to one of the flexor hallucis brevis tendons.

For the purposes of promoting an understanding of the principles of the invention, reference will now be made to the preferred embodiments of the invention as illustrated in the drawings and specific language will be used to describe the same. It will nevertheless be understood that no limitation of the scope of the invention is thereby intended.

Figure 2:
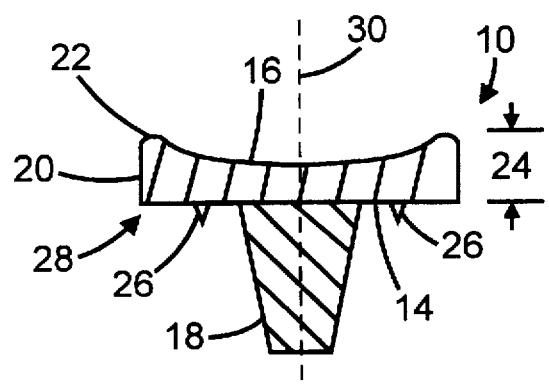
FIG. 2 is a cross-sectional side view in accordance with the preferred embodiment of the implant of FIG. 1 taken along the lines 2—2.
Figure 3:
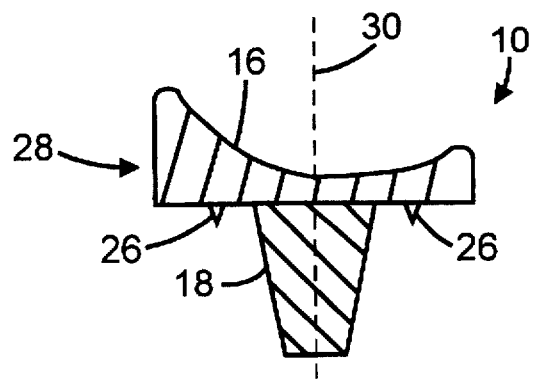
FIG. 3 is a cross-sectional side view in accordance with an alternative embodiment of the implant of FIG. 1 taken along the lines 2—2.

Referring to FIGS. 1–3, a great toe implant 10 has a bearing portion 28 coupled to a step portion 18. Bearing portion 28 has a substantially concave depression in a front face of implant 10 that defines a substantially reniform bearing surface 16 that is intended to contact and articulate with the head of a metatarsal in the great toe joint. Bearing surface 16 has a recess 12 for receiving the flexor hallucis longus tendon once implant 10 is surgically implanted. Bearing surface 16 is coupled to a side surface 20 with a rounded edge 22. Note that the dimension 24 defines the thickness of bearing portion 28 of implant 10 and is preferably as small as possible. The actual dimensions will depend on the specific materials used and the desired function and durability of implant 10. Implant 10 is generally placed in the proximal phalanx of a great toe joint, and has a stem portion 18 extending rearwardly from rear face 14. FIG. 2 shows the cross-sectional view of implant 10 in accordance with the preferred embodiment, which shows an implant that is substantially symmetrical about its longitudinal axis 30. FIG. 3 shows an alternative embodiment that may be used during hallux valgus surgery (i.e., for a proximal phalanx that is not aligned straight with the metatarsal of the great toe joint). As shown in FIG. 3, this embodiment is asymmetrical about the implant's longitudinal axis 30.

Implant 10 preferably includes retaining portions 26 extending from a rear face 14 of implant 10 for inhibiting the rotational movement of implant 10 once surgically implanted into the proximal phalanx. Retaining portions 26 are depicted in FIGS. 2, 3 and 5 as conical spikes, but retaining portions 26 may be any suitable shape or configuration. Regardless of their specific configuration, retaining portions 26 protrude from rear face 14 and engage the proximal phalanx, thereby preventing the rotation of implant 10. Installing implant 10 thus requires aligning the implant in the proper rotational orientation, then driving the retaining portions 26 into the proximal phalanx to retain implant 10 in its rotational position.

FIGS. 4 and 5 illustrate holes 40 in the lower edge of implant 10 that extend from the lower edge 46 to the rear face 14. The lower edge 46 comprises the lower portion of the side surface 20 (FIG. 2). In the preferred embodiment, there are two holes provided that are positioned to allow implant 10 to be attached with a suture to the two flexor hallucis brevis tendons that run underneath the great toe joint.

Referring to FIG. 6, a great toe joint 60 comprises a phalangeal portion 62 and a metatarsal portion 64. Phalangeal portion 62 is shown with a proximal phalanx 52 that has implant 10 surgically implanted. The stem 18 of implant 10 is implanted into the proximal phalanx 52. The length of stem 18 must be sufficient to allow implant 10 to be anchored into proximal phalanx 52. Stem 18 may extend into the medullary canal of the bone in some instances to accomplish sufficient device anchoring.

Metatarsal portion 64 suitably comprises a metatarsal 54 with a rounded head portion 56. In the preferred use of implant 10, metatarsal head portion 56 is the natural surface of metatarsal 54 (as would be the case for phalangeal hemi-joint replacement). However, it is equally within the scope of the invention to use implants on metatarsal 54 that provide a rounded artificial surface that articulates on implant 10 (as would be the case for complete joint replacement using implant 10 on the proximal phalanx).

FIG. 6 illustrates the benefit of providing holes 40 in implant 10. Before installing implant 10 into the proximal phalanx 52, a hole 42 is drilled in proximal phalanx 52 that will align with a hole 40 on implant 10 when implant 10 is surgically implanted. Implant 10 is then implanted into proximal phalanx 52. Surgical suture material 50 is then placed through hole 40 and hole 42, and is sutured to the neighboring flexor hallucis brevis tendon 66. Providing one or more holes 40 in implant 10 provides a significant advantage over the prior art by allowing implant 10 to be attached to neighboring tendons, thereby providing greater joint integrity.

The best mode of the invention relates to replacement of a portion of a proximal phalanx in a great toe joint. A human great toe joint has a proximal phalanx that articulates on a metatarsal. A hemi-joint replacement of the great toe joint is typical when the socket portion of the proximal phalanx has deteriorated but the metatarsal head is largely intact. The surgical procedure for implanting implant 10 is described below for the specific case of a hemi-joint replacement for a great toe joint.

Figure 7:
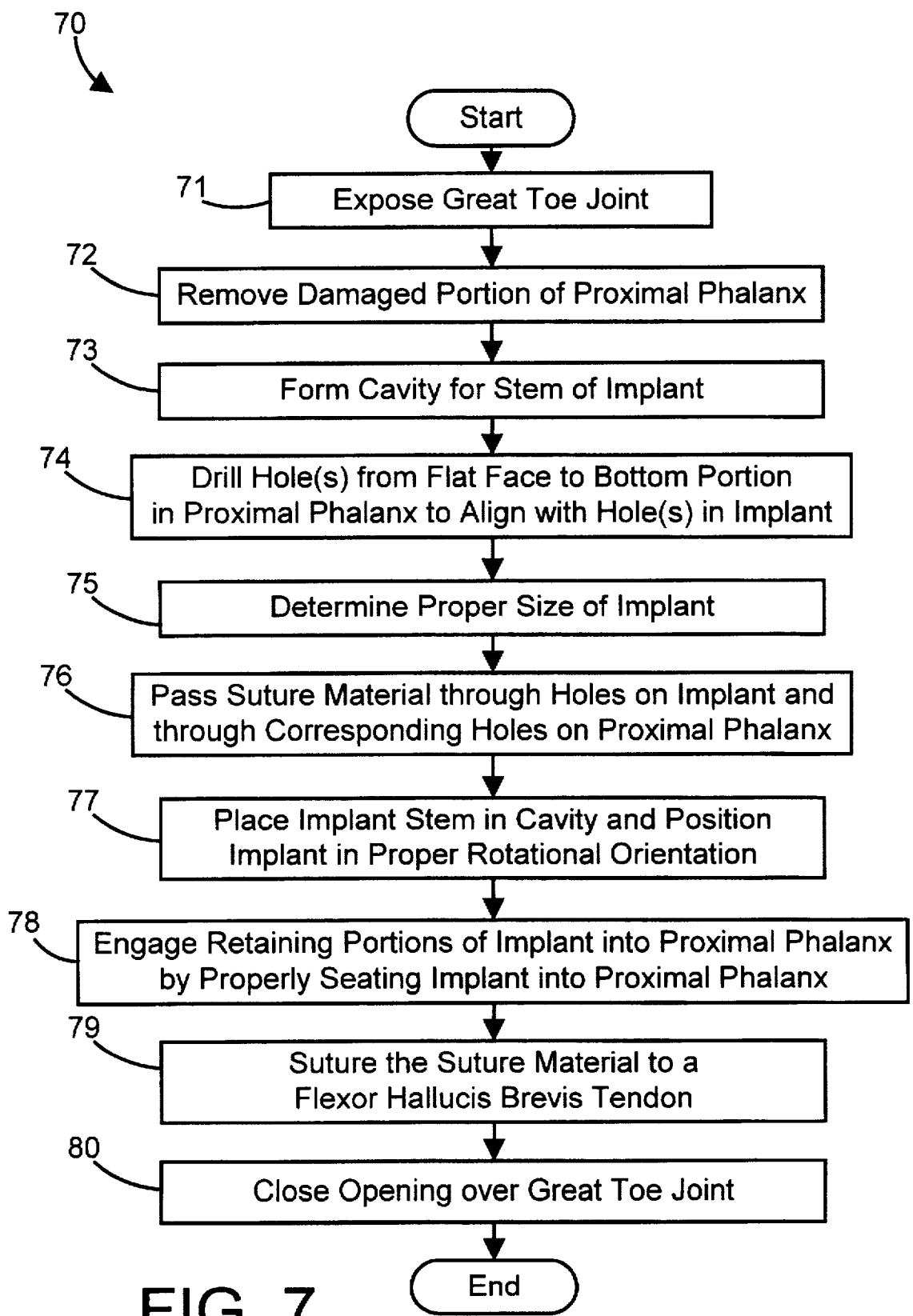
FIG. 7 is a flow diagram of a surgical procedure in accordance with the present invention.

Referring to FIGS. 6 and 7, the surgical procedure 70 for implanting the implant 10 in accordance with the present invention begins by making an incision above the great toe joint such that the great toe joint is exposed (step 71). The damaged portion of proximal phalanx 52 is then removed (step 72), typically by making a cut normal to the longitudinal axis 68 of proximal phalanx 52. The cut is made to accommodate implant 10 which will replace the degenerated portion of proximal phalanx 52. The medullary canal of proximal phalanx 52 is then enlarged (step 73) to create a cavity that will receive stem portion 18 of implant 10. One or more holes 42 are drilled (step 74) from the flat face (i.e., cut edge) of proximal phalanx 52 to the bottom surface of proximal phalanx 52 in positions that will align with the one or more holes 40 on implant 10 when implant 10 is in place. Next, different sizers are placed in the cavity one by one to determine the proper size of implant 10 needed (step 75). At this point, suture material is passed through each hole 40 and the corresponding hole 42 in proximal phalanx 52 (step 76). Stem 18 of a proper sized implant 10 is then placed within the cavity of proximal phalanx 52 and positioned in the proper rotational orientation (step 77). When the surgeon has achieved the proper rotational position of bearing surface 16 with respect to proximal phalanx 52, a force is applied to drive retaining portions 26 into proximal phalanx 52 to hold implant 10 in the proper rotational orientation (step 78). This is typically done by tapping on the implant until the rear face 14 of implant 10 is securely seated against the flat portion of proximal phalanx 52. The surgeon then attaches the suture material 50 that is routed through hole 40 and hole 42 to a neighboring flexor hallucis brevis tendon (step 79). Once implant 10 has been properly implanted into proximal phalanx 52, well-known surgical steps are performed to close the opening over the great toe joint (step 80).

Variations in the Preferred Embodiment

The present invention anticipates the use of any type of material in manufacturing implant 10. For example, titanium, gortex, or silicone may be suitable, along with other materials not specifically discussed herein. Additionally, it is contemplated to form different parts of implant 10 out of differing materials. For example, the bearing portion 28 could be titanium coupled to a silicone stem 18.

One skilled in the art will also understand that implant 10 could be made of two or more separate pieces. For example, stem 18 could be separate from bearing portion 28, and could be attached by any know means such as screws. In addition, while stem 18 and bearing portion 28 are shown in the figures as separate portions of device 10, these different features are shown separately for purposes of illustrating and describing the invention, and in the preferred embodiment device 10 is formed in a single piece.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implant for replacing a portion of a proximal phalanx in a great toe joint, the implant comprising a substantially reniform bearing surface for contacting a metatarsal in the great toe joint, the implant further comprising:

a rear portion coupled to the substantially reniform bearing surface, the rear portion configured to be permanently attached to the proximal phalanx;

a side surface coupling the substantially reniform bearing surface to the rear portion; and at least one hole extending between the side surface and the rear portion.

2. An implant for replacing a portion of a proximal phalanx in a great toe joint overlying a flexor hallucis longus tendon, the implant comprising:

a substantially concave bearing surface having a recess for receiving the flexor hallucis longus tendon when the implant is surgically implanted into the proximal phalanx.

3. The implant of claim 2 further comprising:

a side portion; and a rounded edge coupling the side portion to the substantially concave bearing surface.

4. An implant for replacing a portion of a proximal phalanx in a great toe joint, the implant comprising:

a substantially concave bearing surface;

a rear portion coupled to the substantially concave bearing surface, the rear portion configured to be permanently attached to the proximal phalanx;

a side surface coupling the substantially concave bearing surface to the rear portion;

at least one hole extending between the side surface and the rear portion.

5. The implant of claim 4 wherein the at least one hole is positioned to be in proximity to at least one flexor hallucis brevis tendon when the implant is surgically implanted in the proximal phalanx to allow the implant to be attached to the at least one flexor hallucis brevis tendon by routing a suture through the at least one hole and into the corresponding flexor hallucis brevis tendon.

6. The implant of claim 4 further comprising:

a rounded edge coupling the side surface to the substantially reniform bearing surface.

7. An implant for replacing a portion of a proximal phalanx in a great toe joint, the implant comprising:

(a) a substantially reniform bearing surface defined by a substantially concave depression within a front face of the implant;

(b) a rear portion coupled to the front face for permanent attachment of the implant to the proximal phalanx, the rear portion including:

a rear face;

a stem portion coupled to the rear face and extending rearwardly therefrom, thereby defining a longitudinal axis of the stem portion; and at least one retainer portion coupled to the rear face and extending rearwardly therefrom for engaging the proximal phalanx when the implant is surgically implanted to avoid rotation of the implant relative to the proximal phalanx;

(c) a side portion coupling the front face to the rear portion;

(d) a rounded edge coupling the side portion to the front face;

(e) at least one hole extending between the side surface and the rear portion; and (f) wherein the front face of the implant lies in a plane substantially normal to the longitudinal axis of the stem portion.

8. The implant of claim 7 wherein each retainer portion comprises a substantially conical spike extending rearwardly from the rear face.

9. The implant of claim 7 wherein the substantially reniform bearing surface comprises a recess for receiving a flexor hallucis longus tendon when the implant is surgically implanted into the proximal phalanx.

\* \* \* \* \*